United States Patent
McElroy (10) Patent No.: US 8,522,813 B2
(45) Date of Patent: Sep. 3, 2013

(54) NEEDLELESS SAMPLING PORT

(75) Inventor: Geoffrey R. McElroy, Auburn, MA (US)

(73) Assignee: Covidien LP, Mansfield, MA (US)

( * ) Notice: Subject to any disclaimer, the term of this patent is extended or adjusted under 35 U.S.C. 154(b) by 348 days.

(21) Appl. No.: 12/877,473

(22) Filed: Sep. 8, 2010

(65) Prior Publication Data

US 2012/0055271 A1    Mar. 8, 2012

(51) Int. Cl.
*F16L 37/28* (2006.01)
*A61M 5/00* (2006.01)

(52) U.S. Cl.
USPC ............ 137/317; 251/149.4; 251/149.8; 251/331; 604/249; 604/323

(58) Field of Classification Search
USPC ............ 137/317; 251/331, 149.1–149.5, 251/149, 149.8; 604/249, 256, 323
See application file for complete search history.

(56) References Cited

U.S. PATENT DOCUMENTS

| | | | | |
|---|---|---|---|---|
| 3,930,413 A | * | 1/1976 | Laird et al. ............... | 137/317 |
| 4,116,227 A | | 9/1978 | Eisenberg et al. | |
| 4,533,354 A | | 8/1985 | Jensen | |
| 4,815,477 A | | 3/1989 | McWhorter et al. | |
| 4,927,605 A | | 5/1990 | Dorn et al. | |
| 5,342,316 A | | 8/1994 | Wallace | |
| 5,360,413 A | | 11/1994 | Leason et al. | |
| 5,573,516 A | * | 11/1996 | Tyner ....................... | 604/256 |
| 5,616,138 A | | 4/1997 | Propp | |
| 5,620,434 A | * | 4/1997 | Brony ....................... | 604/249 |
| 5,810,768 A | | 9/1998 | Lopez | |
| 5,919,146 A | | 7/1999 | Propp | |
| 6,083,194 A | * | 7/2000 | Lopez ........................ | 604/256 |
| 6,428,520 B1 | * | 8/2002 | Lopez et al. ............... | 604/249 |
| 6,482,190 B1 | | 11/2002 | Genese et al. | |
| 6,716,200 B2 | | 4/2004 | Bracken et al. | |
| 7,314,061 B2 | * | 1/2008 | Peppel ....................... | 251/149.1 |
| 7,867,204 B2 | * | 1/2011 | Bartholomew et al. ...... | 604/323 |
| 8,100,866 B2 | * | 1/2012 | Peppel ....................... | 604/256 |
| 2006/0213563 A1 | | 9/2006 | Peppel | |

(Continued)

FOREIGN PATENT DOCUMENTS

WO    WO 2008/048777 A2    4/2008

OTHER PUBLICATIONS

Examination Report dated Aug. 24, 2012 issued by the Australian Patent Office in counterpart Australian Application No. 2011221397. (5 pages).

(Continued)

*Primary Examiner* — Kevin Lee
(74) *Attorney, Agent, or Firm* — Lisa E. Winsor, Esq.

(57) ABSTRACT

A sampling port includes a housing and a valve assembly. The housing includes an internal passage through which fluids flow and defines a port in fluid communication with the internal passage. The valve assembly is mountable adjacent the port of the housing and includes a bezel having a channel extending therethrough and a bladder mounted adjacent the bezel. The bladder includes a bladder base and a bladder stem depending from the bladder base which is at least partially received within the channel of the bezel. The bladder stem is movable within the channel of the bezel between a first position substantially preventing fluid flow through the valve assembly and a second position in which a fluid path is established through the valve assembly and in fluid communication with the internal passage of the housing.

16 Claims, 5 Drawing Sheets (56) References Cited

U.S. PATENT DOCUMENTS

2006/0217671 A1 9/2006 Peppel
2007/0060872 A1 3/2007 Hall et al.
2007/0203463 A1 8/2007 Salvadori et al.
2007/0260195 A1 11/2007 Bartholomew

OTHER PUBLICATIONS

Translated Examination Report dated Jan. 10, 2013 issued by the Japanese Patent Office in counterpart Japanese Application No. 2011-195032.

* cited by examiner

NEEDLELESS SAMPLING PORT

BACKGROUND

1. Technical Field

The present disclosure relates generally to a fluid sampling port and, more particularly, to a needleless fluid sampling port.

2. Background of Related Art

Urinary catheterization to drain a patient's bladder and collect urine samples for laboratory analysis are well known in the art. A urine collection system typically includes a urinary catheter connected to a collection/drainage device. In some cases, in order to obtain a sample for laboratory analysis, samples are extracted using syringes or hypodermic needles, which are inserted through walls of the drain tubing. In other cases, samples are obtained by piercing a rubber port on the collection bag or by draining fluid from the collection bag through an outlet port. Such sampling techniques expose medical personnel to potential needle-stick injury and to urine contact. Moreover, such sampling techniques run the risk of contamination of the fluid within the collection system, and thus exposing a patient to potential infections.

Further, various needleless sampling ports may be used. However, these needleless sampling ports include many parts, which can fail and are more complicated and expensive to manufacture. Also, such needleless sampling ports tend to be of a larger profile, which may become caught or entangled on objects during use.

SUMMARY

In accordance with an embodiment of the present disclosure, there is provided a sampling port for use in a biological fluid distribution system, including a housing having an internal passage through which biological fluids flow and defining a port in fluid communication with the internal passage. The sampling port further includes a valve assembly mountable adjacent the port of the housing. The valve assembly includes a bezel having a channel extending therethrough and a bladder mounted adjacent the bezel. The bladder includes a peripheral bladder base and an inner bladder stem depending from the bladder base. The inner bladder stem is at least partially received within the channel of the bezel. The bladder stem is movable within the channel of the bezel between a first position substantially preventing fluid flow through the valve assembly and a second position in which a fluid path is established through the valve assembly and in fluid communication with the internal passage of the housing to thereby permit removal of a fluid sampling through the port. The bladder base includes at least one opening dimensioned to permit passage of fluid as a component of the fluid path when the bladder stem is in the second position thereof.

In an embodiment, the bladder base may be in at least partial contacting relation with the bezel when the bladder stem is in the first position whereby the at least one opening is substantially closed against the bezel. However, the bladder base is at least partially displaced when the bladder stem is in the second position whereby the at least one opening is spaced from the bezel to permit passage of fluid therethrough.

In an embodiment, the bezel may include at least one internal rib surrounding the channel and dimensioned to permit passage of the fluids as a component of the fluid path when the bladder stem is in the second position. The bladder stem may include a notched segment such that the notched segment is in fluid communication with the internal rib when the bladder stem is in the second position in order to permit passage of fluid as a component of the fluid path. Moreover, the bladder base may include an elastic material and may be dimensioned and adapted to stretch upon movement of the bladder stem toward the second position thereof.

In another embodiment, the channel of the bezel is dimensioned to receive a tip segment of a syringe. The tip segment of the syringe engages the bladder stem to move the bladder stem to the second position thereof. The bladder base may include a plurality of openings dimensioned to permit passage of fluid as components of the fluid path when the bladder stem is in the second position thereof. The bladder base and the bezel may define a reservoir for accommodating fluid as a component of the fluid path when the bladder stem is in the second position. The housing may include a housing recessed segment adjacent the port. The valve assembly is at least partially received within the housing recessed segment.

In an embodiment, the bezel may include a first inner surface adjacent the valve assembly and a second outer surface. The channel extends through the inner and outer surfaces. The inner surface of the bezel may include a peripheral recess and the bladder base may include a peripheral ring dimensioned for reception within the peripheral recess.

In accordance with another aspect of the present disclosure, there is provided a sampling port for use in a biological fluid distribution system, including a housing defining a longitudinal axis and having an internal longitudinal passage through which biological fluids flow and a valve housing segment defining a port in fluid communication with the internal passage. The sampling port further includes a valve assembly mountable within the valve housing segment of the housing. The valve assembly includes a bezel and a bladder. The bezel includes a first inner surface and an opposed second outer surface. Moreover, the bezel defines a channel through the first and second surfaces for reception of a syringe tip of the distribution system. The bezel further defines a plurality of axial recesses coaxially arranged about an axis of the channel and disposed adjacent the first inner surface. The bladder includes a peripheral bladder base mounted adjacent the first inner surface of the bezel and an inner bladder stem depending from the bladder base toward the second outer surface of the bezel to be at least partially received within the channel of the bezel. The bladder base includes a plurality of openings extending therethrough. The bladder stem includes a stem wall and has a notch within the stem wall displaced from the bladder base. The bladder stem is movable within the channel of the bezel upon reception of a syringe tip from a first sealed position substantially preventing fluid flow to a second open position in which a fluid path is established through the openings of the bladder base, through the axial recesses of the bezel and the notch of the bladder stem to permit removal of a fluid sampling through the syringe tip.

BRIEF DESCRIPTION OF THE DRAWINGS

The above and other objects and features of the present disclosure will become apparent from the following description of embodiments given in conjunction with the accompanying drawings, in which.

DETAILED DESCRIPTION

Various embodiments of the presently disclosed biological fluid collection system will now be described in detail with reference to the drawings, wherein like reference numerals identify similar or identical elements. In the drawings and in the description that follows, the term "proximal," will refer to the end of a device or system that is closest to the operator, while the term "distal" will refer to the end of the device or system that is farthest from the operator.

Figure 1:
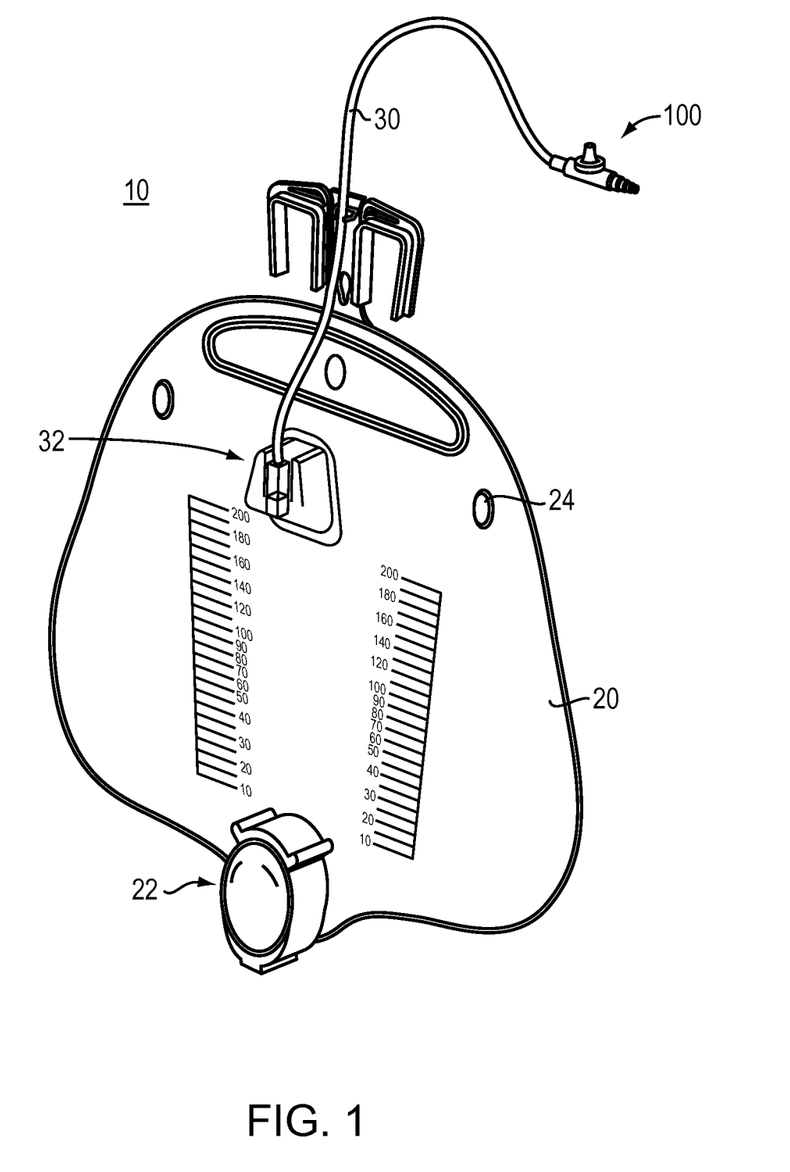
FIG. 1 is a perspective view of a biological fluid collection device incorporating a sampling port in accordance with the present disclosure.

A biological fluid collection device is illustrated in FIG. 1 and is designated by the reference numeral 10. Fluid collection device 10 is used to collect fluid from a catheterized patient. Biological fluid collection device 10 includes a sampling port 100, a fluid collection bag 20, and a drain tube 30 fluidly interconnecting sampling port 100 and fluid collection bag 20. The fluid flows via a transfer tube (not shown) through sampling port 100 and into fluid collection bag 20 via drain tube 30. Drain tube 30 may include an anti-reflux valve 32 that restricts the back flow of fluid from collection bag 20 back into drain tube 30. Anti-reflux valve 32 can be secured to collection bag 20. Fluid collection bag 20 may further include a discharge valve 22 to selectively drain the fluid from collection bag 20. In addition, a vent opening 24 may be provided to let air into collection bag 20 to facilitate draining of the fluid from collection bag 20.

Figure 2:
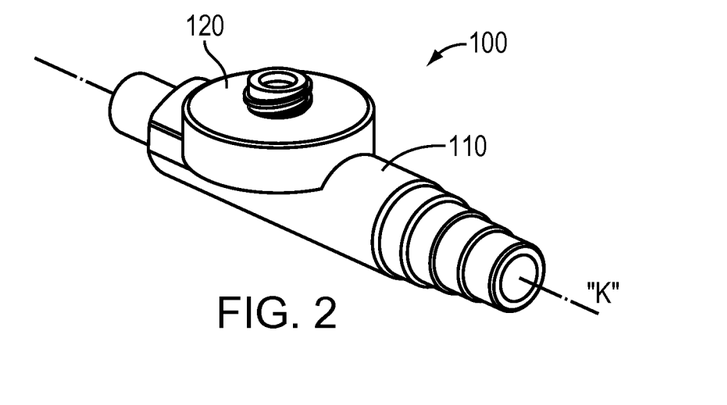
FIG. 2 is a perspective view of a sampling port for use with the collection device of FIG. 1.
Figure 3:
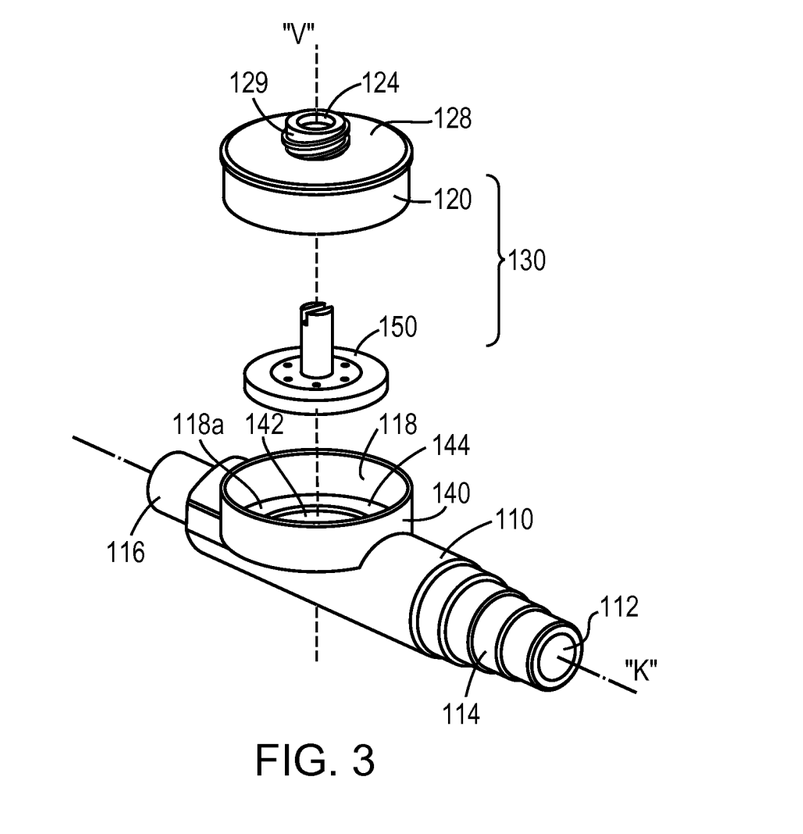
FIG. 3 is a perspective view of the sampling port of FIG. 2 with various components separated.
Figure 4:
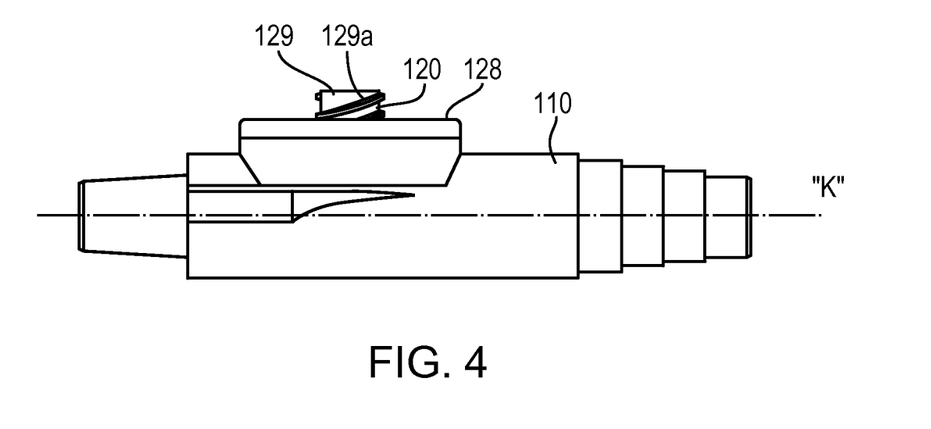
FIG. 4 is side plan view of the sampling port of FIG. 2.

Referring now to FIGS. 2-4, sampling port 100 includes a housing 110 and a valve assembly 130 which is mountable to housing 110. Housing 110 defines longitudinal or housing axis "k" and longitudinal channel 112 which permits passage of the biological fluid through housing 110. Housing 110 includes inlet end 114 and outlet end 116 each for reception of tubing which is part of the fluid collection device 10. Inlet and outlet ends 114, 116 may include ridged surfaces or be stepped to enhance frictional engagement with the tubing. Either or both of inlet and outlet ends 114, 116 may include a circumferential wall segment for reception of the end of the tubing.

Housing 110 further includes valve housing segment 140 which receives valve assembly 130. In an assembled condition, bezel 120 encloses bladder 150 in valve housing segment 140. Valve housing segment 140 includes transverse annular wall segment 118 arranged to define central port 142 and longitudinal wall segment 144. Central port 142 is fluidly couplable with longitudinal channel 112 of housing 110. Valve housing segment 140 may further include a circumferential recess 118a within longitudinal wall segment 144. Circumferential recess 118a facilitates mounting of valve assembly 130 to valve housing segment 140.

Figure 5:
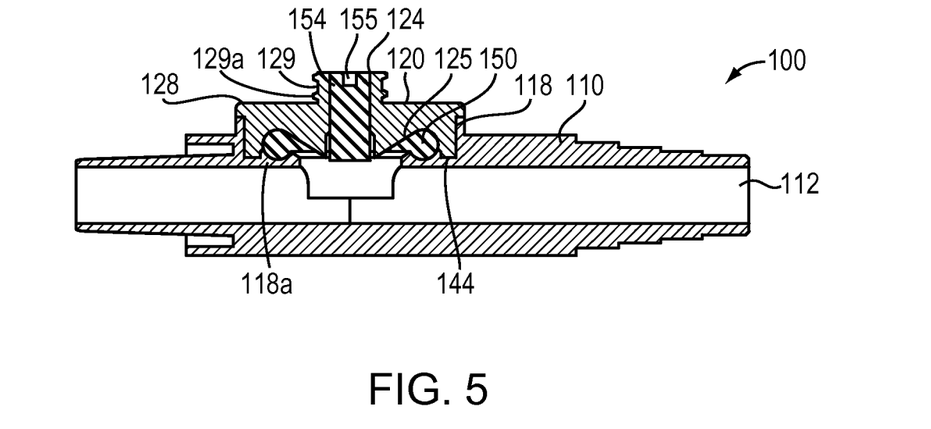
FIG. 5 is a side cross-sectional view of the sampling port of FIG. 2.
Figure 6A:
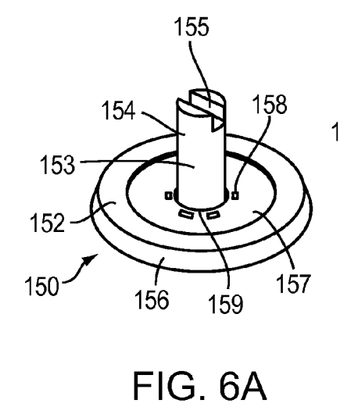
FIGS. 6A-C are perspective views of a bladder of the sampling port in accordance with an embodiment of the present disclosure in various stages or positions of operation.

Referring now to FIGS. 3, 5, 6A and 7, valve assembly 130 includes bladder 150 and bezel 120. Bladder 150 includes bladder base 152 and bladder stem 154 which depends from the bladder base 152, as best illustrated in FIG. 6A. Bladder base 152 includes outer ring 156 and inner bladder segment 157 which is coterminous with bladder stem 154. At least inner bladder segment 157 of bladder base 152 includes an elastomeric material or membrane to permit the inner bladder segment 157 to stretch during its assembly and use. Bladder base 152 includes one or more openings 158 extending through inner bladder segment 157. Openings 158 permit passage of fluids from longitudinal channel 112 of housing 110. Bladder stem 154 defines outer wall 153 and fluid notch 155 extending through the remote end of bladder stem 154. Bladder stem 154 is more rigid than bladder base 152 and is dimensioned to be engaged by the syringe to actuate valve assembly 130. While bladder stem 154 is shown as a cylindrical shape, bladder stem 154 may be any shape that permits bladder stem 154 to at least partially engage bezel 120 when not actuated, as described below. For example, bladder stem 154 may be frusto-conical or stepped.

Figure 7:
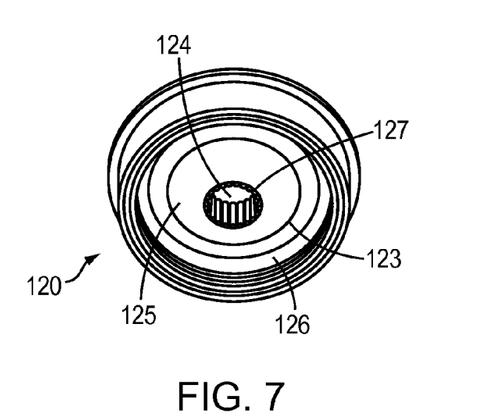
FIG. 7 is a perspective view of a bezel of the sampling port of FIG. 2 in accordance with another aspect of the present disclosure.
Figure 8:
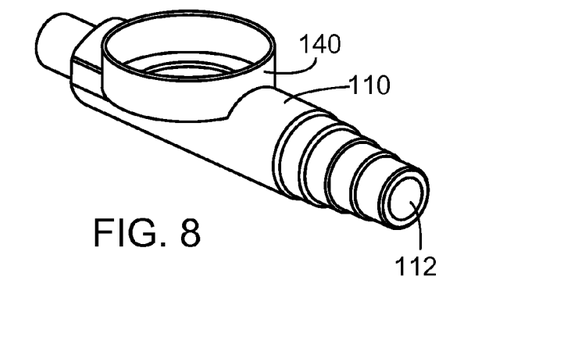
FIG. 8 is a perspective view of a housing of the sampling port of FIG. 2.

Bezel 120 may be a generally disc-shaped member including inner surface 125 and outer surface 128, and having a central channel 124 extending between the inner and outer surfaces 125, 128, as best seen in FIGS. 3 and 7. Inner surface 125 includes peripheral recess 126 and internal area 123 depending inwardly from the peripheral recess 126. Internal area 123 may be tapered or obliquely arranged relative to valve axis "v." Peripheral recess 126 accommodates outer ring 156 of bladder base 152 when in the assembled condition of the components (see FIG. 5). A plurality of axial internal recesses 127 may be arranged about central channel 124 adjacent inner surface 125. Axial internal recesses 127 are a component of the fluid path when the valve assembly 130 is in the actuated position, as discussed below. Alternatively, if bladder stem 154 is a different shape, such as stepped or frusto-conical, the axial internal recesses 127 may not be necessary to provide the fluid path when the valve assembly 130 is in the actuated position.

Bezel 120 and housing 110 are made of a rigid material, such as, for example, plastic (e.g., acrylonitrile butadiene styrene (ABS)), or metal. By making bezel 120 and housing 110 out of the same material, such as ABS, bezel 120 and housing 110 may be ultrasonically welded together. Alternatively, bezel 120 and housing 110 may be connected by any suitable means, such as by chemical welding or adhesives. Housing 110 can be any rigid structure that enables the passage of the fluid through longitudinal channel 112 defined therein, such as the housing of the Covidien SAFEGUARD™ urine sampling port.

Figure 6B:
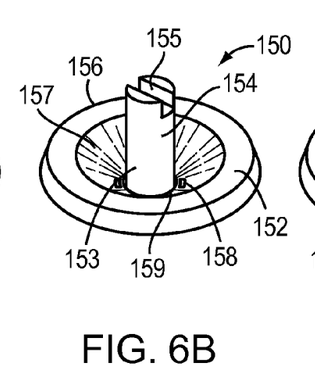
Figure 6C:
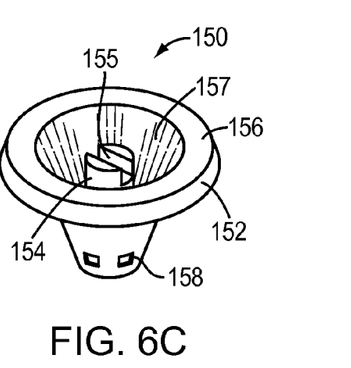

Referring now to FIGS. 6A-C, bladder or valve 150 will be discussed in detail. Bladder 150 may be an element which is filled with air or liquid, and may be selectively filled with a predetermined volume of fluid depending on design objectives. It is also envisioned that bladder 150 may be substantially solid. Bladder 150 may be, for example, an injection molded rubber part, but any other material with characteristics of rubber such as, for example, silicone and latex, may be used for bladder 150. As discussed above, bladder 150 includes bladder base 152 and bladder stem 154 which extends from a center portion of bladder base 152. Bladder base 152 includes inner bladder segment 157 and outer ring 156 which surrounds and reinforces an outer perimeter of inner bladder segment 157. At least inner bladder segment 157 of bladder base 152 includes an elastic material, such as an elastomer, to enable inner bladder segment 157 to stretch during actuation of valve assembly 130. Inner bladder segment 157 may define a plurality of openings 158 uniformly dispersed around the radial perimeter of bladder stem 154. Outer ring 156 is disposed within peripheral recess 126 of inner surface 125 of bezel 120 and circumferential recess 118a of valve housing segment 140, to facilitate secure positioning of bladder 150 in valve housing segment 140, as will be discussed below.

Figure 9:
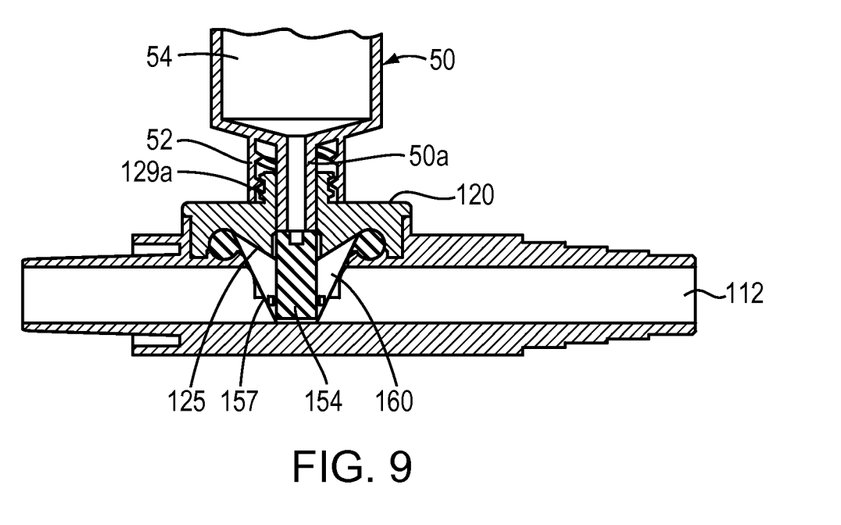
FIG. 9 is a side cross-sectional view of the sampling port of FIG. 5 attached to a syringe.
Figure 10:
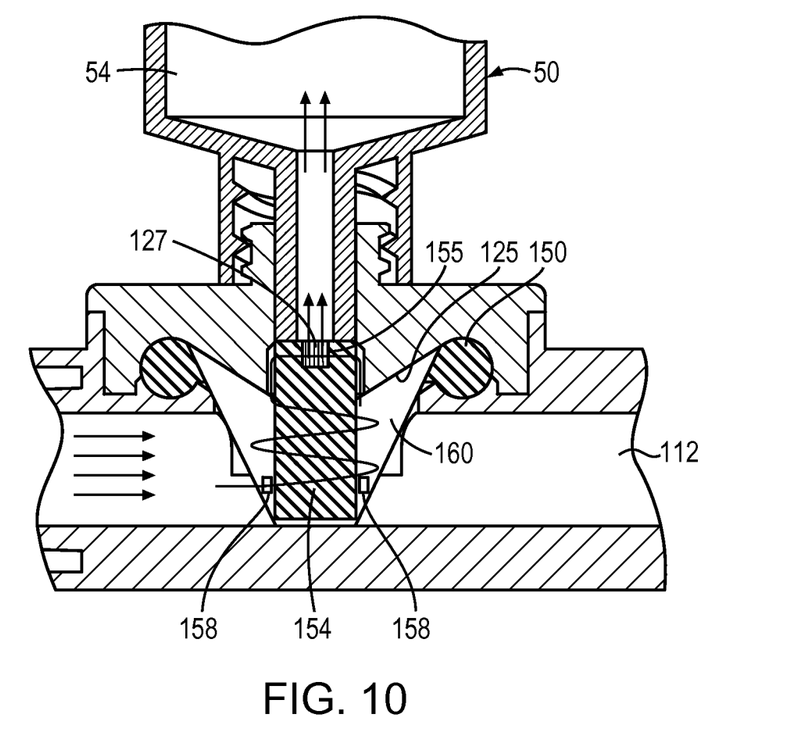
FIG. 10 is a partially enlarged cross-sectional view of the sampling port of FIG. 9.

With continuing reference to FIGS. 6A-6C, the elastic nature of at least inner bladder segment 157 enables bladder 150 to assume various positions, such that bladder stem 154 is movable within central channel 124 of bezel 120 between a first position substantially preventing fluid flow through valve assembly 130 and a second position in which the fluid path is established through valve assembly 130 and in fluid communication with longitudinal channel 112 of housing 110 to thereby permit removal of a fluid sampling through central port 142 of valve housing segment 140. In a neutral position, such as prior to mounting bladder 150 relative to the exemplary housing 110 and there is no force applied to bladder 150, a bottom portion 159 of solid cylindrical bladder stem 154 and bladder base 152 are substantially coplanar with outer ring 156 of bladder base 152, as shown in FIG. 6A. In the first position shown in FIG. 6B, when bladder 150 is disposed within exemplary valve housing segment 140 of housing 110 and substantially in contact against inner surface 125 of bezel 120, a slight downward force may be applied to inner bladder segment 157 by bezel 120, as will be discussed in detail below. In the first position, bottom portion 159 of bladder stem 154 is positioned slightly below outer ring 156 of bladder 150, and inner bladder segment 157 is slightly stretched forming a conical shape. However, fluid notch 155 of bladder stem 154 remains disposed above outer ring 156, as shown in FIG. 6B. In the second position, as shown in FIG. 6C, inner bladder segment 157 assumes an inverted conical shape due to a downward force applied to bladder 150 through bladder stem 154. Under such position, fluid notch 155 of bladder stem 154 is substantially aligned with or positioned slightly below outer ring 156. The flexibility of inner bladder segment 157 of bladder 150 in conjunction with the plurality of openings 158 enables biological fluid to flow into a reservoir 160 defined by the inverse conical configuration of bladder 150, between bladder base 152 and inner surface 125 of bezel 120, as best seen in FIGS. 9 and 10. Thus, when bladder 150 is in the second position as shown in FIG. 6C, bladder 150 permits passage of the fluid therethrough, and when bladder 150 is in the first position as shown in FIG. 6B, bladder 150 in conjunction with bezel 120 blocks passage of the fluid therethrough, as will be described in greater detail below. While specific relative positions of the bladder stem 154, fluid notch 155 and outer ring 156 are disclosed, it can be appreciated that other relative positions are within the scope of the invention and will depend on the specific configuration of the bezel 120 and bladder 150.

According to another aspect of the present disclosure, bezel 120 is shown in FIGS. 3 and 7. Bezel 120 is a fitting that can be attached to a housing, such as, for example, housing 110 shown, or modified to fit other housings, such as the Covidien SAFEGUARD™ urine sampling port housing. Bezel 120 encloses bladder 150 within valve housing segment 140, in a fluid-tight manner. As discussed above, inner surface 125 of bezel 120 may define peripheral recess 126 having a semi-circular cross-section. Peripheral recess 126 partially receives outer ring 156 of bladder base 152. As such, peripheral recess 126 of bezel 120 in conjunction with circumferential recess 118a of valve housing segment 140 forms a peripheral groove having a circular cross-section dimensioned to receive the entire outer ring 156 of bladder 150.

In addition, bezel 120 provides a central channel 124 configured and dimensioned to receive solid cylindrical bladder stem 154 of the exemplary bladder 150. As best illustrated in FIG. 5, bladder 150 is securely positioned within valve housing segment 140 by bezel 120 aided by outer ring 156 that rests in circumferential recess 118a of valve housing segment 140 and peripheral recess 126 of bezel 120, and solid cylindrical bladder stem 154 that is positioned within central channel 124 of bezel 120. The top portion of bladder stem 154 is flush with a top portion of bezel 120 when assembled. Central channel 124 of bezel 120 is dimensioned to receive a tip segment of a syringe, such that the tip segment of the syringe engages bladder stem 154 to move bladder stem 154 to the second position of bladder 150.

With continued reference to FIGS. 5 and 7, inner surface 125 of bezel 120 may be inwardly, downwardly tapered toward central channel 124 and, more specifically, to a bottom portion of central channel 124 from peripheral recess 126. Tapered inner surface 125 of bezel 120 stretches inner bladder segment 157 of bladder 150 downward to create tension upon attachment. The tension helps enable bladder 150 to seal against the tapered inner surface 125 at the first position of bladder 150 and enables bladder stem 154 to fully return to the first position after being depressed down through central channel 124.

With reference to FIGS. 3 and 7, bezel 120 may define a plurality of axial recesses 127 coaxially arranged about an axis "v" of central channel 124 and disposed adjacent inner surface 125. In the alternative, bezel 120 may include at least one internal rib surrounding central channel 124 and dimensioned to permit passage of fluid as a component of the fluid path when bladder stem 154 is in the second position. In particular, biological fluid pulled through openings 158 of inner bladder segment 157 by negative pressure created by the syringe travels through the plurality of axial recesses 127 to fluid notch 155 at the top portion of bladder stem 154, as will be described in greater detail below. Bezel 120 further includes an engagement portion 129 which extends from outer surface 128 of bezel 120, as shown in FIGS. 4 and 5. Engagement portion 129 defines a channel therethough in communication with central channel 124. Furthermore, engagement portion 129 may have a conical taper configuration that enables a tightly sealed attachment with, for example, an ISO 594 compatible luer (as is used on standard syringes). In addition, an exterior surface of engagement portion 129 may include ISO 594 compatible luer lock threads 129a, such that a standard ISO 594 compatible luer lock syringe can be screwed thereon. The luer lock threads 129a in conjunction with the conical taper may provide a fitting fully compatible with ISO 594.

With reference back to FIGS. 3 and 5, assembly of sampling port 100 including housing 110 and valve assembly 130 is described. Initially, an undeformed bladder 150 as described above in FIG. 6A, is placed in valve housing segment 140. In particular, outer ring 156 of bladder 150 is partially received in circumferential recess 118a of housing 110. At this time, bladder 150 encloses central port 142 which serves as a conduit to longitudinal channel 112 through which biological fluid flows. In addition, solid cylindrical bladder stem 154 is concentrically aligned with central port 142. Thereafter, bezel 120 having tapered inner surface 125 is placed over bladder 150 and outer ring 156 of bladder base 152 is placed between circumferential recess 118a of valve housing segment 140 and peripheral recess 126 of bezel 120. Solid cylindrical bladder stem 154 of bladder 150 is movably positioned within central channel 124 of bezel 120. Bladder stem 154 is movable within the central channel 124 of bezel 120 between a first position substantially preventing fluid flow through valve assembly 130 and a second position in which a fluid path is established through valve assembly 130 and in fluid communication with longitudinal channel 112 of housing 110 to thereby permit removal of a fluid sampling through central port 142. Tapered inner surface 125 of bezel 120 may stretch inner bladder segment 157 of bladder 150 downward and into central port 142 to create tension, placing bladder 150 into the first position shown in FIG. 6B. A top portion of solid cylindrical bladder stem 154 is adjacent to a top portion of engagement portion 129 of bezel 120. Inner bladder segment 157 may be stretched and supported against tapered inner surface 125 of bezel 120. A smooth surface of inner surface 125 of bezel 120 may provide a seal against openings 158 defined in inner bladder segment 157 of bladder 150. Providing tension in inner bladder segment 157 may enable bladder 150 to provide a seal at rest and help bladder stem 154 to fully return to its first position after being depressed down through central channel 124, as will be described in detail below.

In the assembled condition of bladder 150, as shown in FIG. 5, a double seal may be created inside sampling port 100 between longitudinal channel 112 and the opening at the top portion of central channel 124 of bezel 120. The first seal may be created by the smooth surface of tapered inner surface 125 of bezel 120 pressed against bladder base 152. Specifically, as bezel 120 is attached to valve housing segment 140, inner bladder segment 157 is stretched by inner surface 125 of bezel 120. The stretched inner bladder segment 157 is pressed against the smooth surface of inner surface 125. As a result, the fluid path through openings 158 defined in inner bladder segment 157 is blocked under normal to high pressure condition within longitudinal channel 112. The second seal is created between solid cylindrical bladder stem 154 of bladder 150 and central channel 124 of bezel 120. Bladder stem 154 and central channel 124 are dimensioned to provide a long flush fit that will block fluid flow under normal pressure conditions. Fluid communication is established when fluid notch 155 of bladder 150 is positioned adjacent the plurality of axial internal recesses 127 coaxially arranged about an axis of central channel 124 of bezel 120.

In operation, biological fluid collection system 10 including sampling port 100 is used in accordance with methods known by those skilled in the art. Stepped portion of housing 110 is connected to a transfer tube (not shown) which is connected to a catheter positioned within the bladder of a patient and the frusta-conical portion is connected to fluid collection bag 20. Sampling port 100 is assembled as shown in FIG. 5, including housing 110 and valve assembly 130. As discussed above, when bladder 150 is in the first position, a double seal may be maintained inside sampling port 100 between longitudinal channel 112 and an opening at the top portion of central channel 124 of bezel 120. To draw a sample, a syringe 50 having a tip 50a, as shown in FIGS. 9 and 10, is connected to sampling port 100. For example, the tip 50a of an ISO 594 compatible luer fitting (luer slip or luer lock syringe) is inserted into bezel 120.

With continued reference to FIGS. 9 and 10, as an inner surface of guide 52 of syringe 50 mates with threads 129a on an outer surface of engagement portion 129 extending from outer surface 128 of bezel 120, tip 50a is inserted into central channel 124 of bezel 120 and pushes solid cylindrical bladder stem 154 downward through central port 142 to or near the bottom surface of longitudinal channel 112. Since outer ring 156 is securely anchored in place within circumferential recess 118A of valve housing segment 140 and peripheral recess 126 of bezel 120 and enclosed by bezel 120, as bladder stem 154 is moved downward into channel 112, inner bladder segment 157 of bladder 150 is stretched by bladder stem 154 now resting at or near the bottom surface of longitudinal channel 112. As a result, bladder 150 at this time has an inverse conical shape, creating reservoir 160 between solid cylindrical bladder stem 154 and inner bladder segment 157.

In particular, openings 158 defined in inner bladder segment 157 are now positioned within longitudinal channel 112, and thus within the stream of biological fluid. During this process, openings 158 that were pressed against the smooth tapered inner surface 125 of bezel 120, and thereby forming a seal, are now positioned within longitudinal channel 112 and provide fluid communication between longitudinal channel 112 and reservoir 160.

With reference still to FIGS. 9 and 10, as tip 50a pushes bladder stem 154 of bladder 150 into longitudinal channel 112, at least the top portion of bladder stem 154 remains inside central channel 124 of bezel 120. However, the top portion of bladder stem 154 including fluid notch 155 now aligns with the plurality of axial internal recesses 127 provided at the bottom portion of central channel 124. As a result, fluid notch 155 of bladder 150 is in fluid communication with reservoir 160 via the plurality of axial internal recesses 127.

At this time, negative pressure is applied to central channel 124 by syringe 50, through the use of plunger 54. The biological fluid flowing through longitudinal channel 112 of housing 110 passes through openings 158 now in communication with longitudinal channel 112. The fluid then fills up reservoir 160 which is in communication with fluid notch 155. Fluid in reservoir 160 is then pulled upward through axial internal recesses 127 of central channel 124 of bezel 120 and continues through fluid notch 155 at the top portion of bladder stem 154 and into syringe 50. The fluid collected in syringe 50 can be used as a sample for laboratory analysis.

When syringe 50 is detached from sampling port 100 and tip 50a is removed from central channel 124, bladder 150 returns to its first position to resume the double-seal condition within sampling port 100, preventing fluid from longitudinal channel 112 from flowing through openings 158 and fluid notch 155.

Sampling port 100 of the present disclosure provides a low-profile configuration. The low-profile design is advantageous in a clinical setting because it is less likely to get caught onto other objects during use. Moreover, it is less likely to interfere with the patient, and thereby reducing injury or discomfort to patient. Furthermore, it is less likely to create an obstacle to a clinician during a medical procedure. In addition, sampling port 100 also offers the benefit of requiring fewer parts than other known biological fluid sampling ports. Such design may reduce manufacturing costs.

It will be understood that various modifications may be made to the embodiments of the presently disclosed sampling port. Therefore, the above description should not be construed as limiting, but merely as exemplifications of embodiments. Those skilled in the art will envision other modifications within the scope and spirit of the present disclosure.

What is claimed is:

1. A sampling port comprising:
    a housing having an internal passage through which a fluid flows and defining a port in fluid communication with the internal passage; and
    a valve assembly mountable adjacent the port of the housing, the valve assembly including:
    a bezel having a channel extending therethrough; and
    a bladder mounted adjacent the bezel, the bladder including a bladder base having a flexible bladder segment, and an inner bladder stem depending from the flexible bladder segment and being at least partially received within the channel of the bezel, the bladder stem being movable within the channel of the bezel between a first position substantially preventing fluid flow through the valve assembly and a second position in which a fluid path is established through the valve assembly and in fluid communication with the internal passage of the housing to thereby permit removal of a fluid sample through the port, the flexible bladder segment including a plurality of openings dimensioned to permit passage of fluid as a component of the fluid path when the bladder stem is in the second position thereof, wherein the plurality of openings are located around a perimeter of and immediately adjacent the bladder stem, wherein the bladder stem provides a first seal to prevent a flow of fluid through the valve assembly when the bladder stem is in the first position, wherein the plurality of openings are sealed against a surface of the bezel to create a second seal to prevent the flow of fluid through the valve assembly when the bladder stem is in the first position, and wherein the plurality of openings are located within the internal passage with the bladder stem in the second position.

2. The sampling port according to claim 1, wherein the bladder base is at least partially displaced when the bladder stem is in the second position whereby the plurality of openings are spaced from the bezel to permit passage of fluid therethrough.

3. The sampling port according to claim 2, wherein the bezel includes at least one internal rib surrounding the channel and dimensioned to permit passage of fluid as a component of the fluid path when the bladder stem is in the second position.

4. The sampling port according to claim 3, wherein the bladder stem includes a notched segment, the notched segment in fluid communication with the at least one internal rib when the bladder stem is in the second position to permit passage of fluid as a component of the fluid path.

5. The sampling port according to claim 4, wherein the bladder base is dimensioned and adapted to stretch the flexible bladder segment upon movement of the bladder stem toward the second position thereof.

6. The sampling port according to claim 1, wherein the channel of the bezel is dimensioned to receive a tip segment of a syringe, the tip segment engaging the bladder stem to move the bladder stem to the second position thereof.

7. The sampling port according to claim 1, wherein the bladder base and the bezel define a reservoir for accommodating fluid as a component of the fluid path when the bladder stem is in the second position.

8. The sampling port according to claim 1, wherein the housing includes a housing recessed segment adjacent the port, the valve assembly at least partially received within the housing recessed segment.

9. The sampling port according to claim 1, wherein the bezel includes an inner surface adjacent the bladder and an outer surface, the channel extending through the inner and outer surfaces.

10. The sampling port according to claim 9, wherein the first inner surface of the bezel includes a peripheral recess and the bladder base includes a peripheral ring dimensioned for reception within the peripheral recess.

11. The sampling port according to claim 1, wherein the plurality of openings includes at least four openings spaced 360 degrees about the perimeter of the bladder stem.

12. A sampling port comprising:
a housing defining a longitudinal axis and having an internal longitudinal passage through which a fluid may flow, the housing including a valve housing segment defining a port in fluid communication with the internal passage; and
a valve assembly mountable within the valve housing segment of the housing, the valve assembly including:
a bezel including an inner surface and an opposed outer surface, the bezel defining a channel through the inner surface and outer surface for reception of a syringe tip, the bezel further defining a plurality of axial recesses coaxially arranged about an axis of the channel and disposed adjacent the inner surface; and
a bladder including a bladder base having a flexible bladder segment mounted adjacent the inner surface of the bezel and a bladder stem depending from the flexible bladder segment toward the outer surface of the bezel to be at least partially received within the channel of the bezel, the flexible bladder segment including a plurality of openings extending therethrough located around a perimeter of and immediately adjacent the bladder stem, the flexible bladder segment sealed against a surface of the bezel to form a first seal to prevent a flow of fluid through the valve assembly when the bladder stem is in a first position, the bladder stem including a stem wall and having a notch within the stem wall displaced from the bladder base, the bladder stem forming a second seal in the channel to prevent the flow of fluid through the valve assembly when the bladder stem is in the first position and being movable within the channel of the bezel upon reception of the syringe tip from the first position to a second position in which a fluid path is established through the plurality of openings, through the axial recesses of the bezel and the notch of the bladder stem to permit removal of a fluid sampling through the syringe tip.

13. The sampling port according to claim 12, wherein the bladder base is at least partially displaced from the inner surface of the bezel when the bladder stem is in the second position whereby the plurality of openings are spaced from the bezel to permit passage of fluid therethrough.

14. The sampling port according to claim 12, wherein the housing segment includes a peripheral recess and the bladder base of the bladder includes a peripheral rim dimensioned for reception into the peripheral recess to facilitate mounting of the valve assembly relative to the housing.

15. The sampling port according to claim 12, wherein the plurality of openings are located within the internal longitudinal passage with the bladder stem in the second position.

16. The sampling port according to claim 12, wherein the plurality of openings includes at least four openings spaced 360 degrees about the perimeter of the bladder stem.

\* \* \* \* \*